(12) United States Patent
Du et al.

(10) Patent No.: US 8,399,511 B2
(45) Date of Patent: Mar. 19, 2013

(54) TWO TYPES OF CRYSTALLINE OF PINOCEMBRIN, THEIR PREPARATION AND THEIR USE FOR MANUFACTURE OF PHARMACEUTICAL COMPOSITIONS

(75) Inventors: Guanhua Du, Beijing (CN); Yang Lv, Beijing (CN); Song Wu, Beijing (CN); Ke Wang, Beijing (CN); Ying Chang, Beijing (CN); Zhihong Yang, Beijing (CN); Yuanfeng Tong, Beijing (CN); Mei Gao, Beijing (CN)

(73) Assignees: CSPC Zhongqi Pharmaceutical Technology (Shijiazhuang) Co., Ltd. (CN); Institute of Materia Medica, Chinese Academy of Medical Sciences (CN)

(*) Notice: Subject to any disclaimer, the term of this patent is extended or adjusted under 35 U.S.C. 154(b) by 0 days.

(21) Appl. No.: 13/128,896

(22) PCT Filed: Nov. 13, 2008

(86) PCT No.: PCT/CN2008/073047
§ 371 (c)(1),
(2), (4) Date: May 12, 2011

(87) PCT Pub. No.: WO2010/054512
PCT Pub. Date: May 20, 2010

(65) Prior Publication Data
US 2011/0213024 A1    Sep. 1, 2011

(51) Int. Cl.
*A61K 31/353* (2006.01)
*C07D 311/32* (2006.01)

(52) U.S. Cl. ......................... 514/457; 549/403

(58) Field of Classification Search .................. 549/403; 514/457
See application file for complete search history.

(56) References Cited

FOREIGN PATENT DOCUMENTS

| CN | 1695608 A | 11/2005 |
|---|---|---|
| CN | 101307044 A | 11/2008 |
| WO | 2007056188 A1 | 5/2007 |

OTHER PUBLICATIONS

Brown, 2006, Electron. J. Environ. Agric. Food Chem., vol. 5, No. 2, p. 1265-1277.*
Hasegawa, 1957, Journal of the American Chemical Society, vol. 79, p. 450-452.*
Lindstedt, 1950, Acta Chem. Scand, vol. 4, p. 55-59.*
Nagahiro, 1998, Journal of Medical Investigation, vol. 45, p. 57-70.*
Rodriguez-Spong, 2004, Advanced Drug Delivery Reviews, vol. 56, p. 241-274.*
Yuan, 2008, Journal of Asian Natural Products Research, vol. 10, No. 10, p. 999-1002.*
Cheng Yonghao, "Optimizing synthetic method of pinocembrin by uniform experiment design" Chemical Research and Application, Nov. 2006, vol. 18, No. 11, pp. 1334-1335.
Ya-bo Duan, "Synthesis and antimicrobial activity in pinocembrin and it's derivatives", Chinese Journal of Medicinal Chemistry, vol. 16., No. 6, p. 342, Dec. 2006.
Thaworn Jaipetch " Constituents of Boesenbergia pandurata (syn. *Kaempferia pandurata*): Isolation, Crystal Structure and Synthesis of Boesenbergin A", Aust. J. Chem., 1982, vol. 35, pp. 351-361.
Otto Richard Gottlieb The Chemistry of Rosewood, II. Isolation and Identification of Cotoin and Pinocembrin, Journal of the American Chemical Society, May 1958, vol. 80. No. 9, pp. 2263-2265.
International Search Report PCT/CN2008/073047: Dated Aug. 13, 2009.
Cheng Yonghao., "synthesis of 5, 7-dihydroxyflavanone, chemical reagents", 2006, 28(7): 437-438.
Yoshinori Asakawa: "Chemical Constituents of *Alnus sieboldiana* (Betulaceae) II. The Isolation and Structure of Flavanoids and Stilbenes", Bulletin of the Chemical Society of Japan, vol. 44, No. 10, Jan. 1, 1971, pp. 2761-2766.
Brule D. et al: "Sur une methode permettant de preparer des flavones marquees au carbone 14", Comptes Rendus Hebdomadaires Des Seances De L'Academie Dessciences, Gauthier-Villars, Paris, FR, Jan. 11, 1960, pp. 365-367
Donelly D. et al: "Dalbergia Species. Part IX. Phytochemical Examination of Dabergia stevensonii Standl", Journal of the Chemical Society, Perkin Transactions 1, Chemical Society, GB, Jan. 1, 1973, pp. 1737-1745.
Extended European Search Report for Application No./Patent No. 08878072.1-2117/2360152, dated May 2, 2012.
Hiroshi Fukui et al: "Two Antimicrobial Flavanones from the Leaves of *Glycyrrhiza glabra*", Chemical & Pharmaceutical Bulletin, Pharmaceutical Society of Japan, vol. 36, No. 10, Jan. 1988, pp. 4174-4176.
Thomas Munson Harris et al.: Journal of the American Chemical Society, vol. 89, No. 25, Dec. 6, 1967, pp. 6734-6741.
Yang Huan et al.: "Flavanoid aglycones of *Oxytropis falcata*", Chemistry of Natural Compounds, vol. 45, No. 2, Mar. 1, 2009, pp. 239-241.

(Continued)

*Primary Examiner* — Golam M M Shameem
*Assistant Examiner* — Karen Cheng
(74) *Attorney, Agent, or Firm* — Cantor Colburn LLP (57) ABSTRACT

Two crystalline forms of pinocembrin of formula (I): α and β, their preparation and their use for manufacture of pharmaceutical compositions. There exists difference between them in bioavailability. They are used for treating and preventing cerebral ischemic diseases by protective action of neurovascular unit, and enhancing blood drug level in vivo.

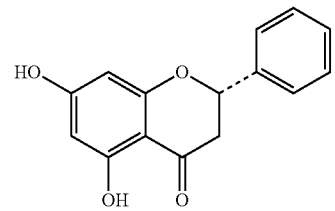

9 Claims, 4 Drawing Sheets

OTHER PUBLICATIONS

Ishimatsu M. et al. "Alnusnins A and B from the leaves of *Alnus sieboldiana*", Phytochemistry, Pergamon Press, GB, vol. 28, No. 11, Jan. 1, 1989, pp. 3179-3184.

Katerere D.R. et al: "Cyclobutanes from *Combretum albopunctatum*", Phytochemistry, Pergamon Press, GB, vol. 65, No. 4, Feb. 1, 2004, pp. 433-438.

Yasuo Komoda: "Isolation of Flavonoids from *Populus nigra* as delta4-3-Ketosteroid (5alpha) Reductase Inhibitors", Chemical & Pharmaceutical Bulletin, vol. 37, No. 11, 1989, pp. 3128-3130.

Kuroyanagi et al: "Studies on the Constituents of the Seeds of Alpinia katsumadai Hayata", Chemical & Pharmaceutical Bulletin, vol. 31, No. 5, 1983, pp. 1544-1550.

L.A. Onuchak et al.: "HPLC analysis of Artemisia dracunculus extracts", Chemistry of Natural Compounds, vol. 36, No. 2, Mar. 1, 2000, pp. 144-147.

Ribas I. et al: "Estudio de un glucosido aislado de las hojas del sarthamnus commutatus Willk. de Galicia", Anales De La Real Sociedad Espanola De Fisica Y Quimica, Serie B: Quimica, Madrid, ES, vol. 52, Jan. 1, 1956, pp. 271-280.

Rosenmund and Margarethe Rosenmund KW: "Uber die Synthese des Naringenins and Phloretins", Chemische Berichte, Verlag Chemie Gmbh, Weinheim, DE, vol. 61, No. 11, Jan. 1, 1928, pp. 2608-2612.

Sachdev K. et al. "Flavonoids from *Dodonaea viscosa*", Phytochemistry, Pergamon Press, GB, vol. 22, No. 5, Jan. 1, 1983, pp. 1253-1256.

Shinoda J. et al: "Uber die Synthese der Polyoxychalkone, -hydrochalkone und -flavanone", Chemisches Zentralblatt, Berlin: Akademie-Verlag, vol. 99, Jan. 1, 1928, p. 1885.

M.P. Yuldashev: Chemistry of Natural Compounds, vol. 37, No. 3, Jan. 1, 2001, pp. 224-225.

* cited by examiner

TWO TYPES OF CRYSTALLINE OF PINOCEMBRIN, THEIR PREPARATION AND THEIR USE FOR MANUFACTURE OF PHARMACEUTICAL COMPOSITIONS

FIELD OF INVENTION

The present invention relates to two crystalline forms of the compound pinocembrin, and active pharmaceutical ingredients, pharmaceutical compositions and dosage forms containing the two crystalline forms of pinocembrin, and the use thereof for manufacture of pharmaceutical compositions and treating diseases, and the method for preparing the two crystalline forms of pinocembrin.

BACKGROUND OF THE INVENTION

Pinocembrin (chemical name: 5,7-dihydroxy-2-phenyl-4-chromanone) is a flavone compound, widely found in the nature. Its chemical structure is as below:

exiting in l-isomer, d-isomer, l-isomer- or d-isomer-enriched mixture, and racemate.

Previous pharmacological experiments showed that pinocembrin had strong bacteriostasis, antivirus, and antifungal activities. For example, honey, a Chinese traditional health care food, is rich in pinocembrin. So eating honey sugar frequently is not only harmless to the teeth, but also can sterilize the oral cavity, for example, relieving oral ulcer and accelerating wound healing. Chinese Patent CN1695608A, titled "Use of pinocembrin for manufacture of pharmaceutical compositions for preventing and treating diseases related to nerve cell injury"[1], disclosed the use of pinocembrin for manufacture of pharmaceutical compositions for preventing or treating diseases related to cerebral ischemia, sequelae of cerebral ischemia, nerve cell injury and function alteration.

DESCRIPTION OF THE INVENTION

It was found surprisingly by the inventors that pinocembrin had two different crystalline forms α and β, and the inventors developed the preparations thereof. The inventors also found that there was a significant difference between the two crystalline forms in the uptake by organism, wherein the uptake rate of β crystalline form was greater than that of α crystalline form, for example, the uptake rate of β crystalline form can be 2 times or more greater than that of α crystalline from. The biological activities thereof in medicament therapy are different due to differences in drug blood concentrations.

One embodiment of the present invention provides α crystalline form, β crystalline form, or the mixture of α crystalline form and β crystalline form in different proportions, with respect to pinocembrin. Preferably, these crystalline forms or the mixture thereof contains no crystal water or other organic solvents.

One embodiment of the present invention provides the method for preparing α crystalline form, β crystalline form, or the mixture of α crystalline form and β crystalline form of pinocembrin in different proportions.

One embodiment of the present invention provides a pharmaceutical composition comprising pure α crystalline form, pure β crystalline form, or the mixture of α crystalline form and β crystalline form of pinocembrin in different proportions. The pharmaceutical composition can also comprise one or more pharmaceutically acceptable carriers. There is no limitation on the pharmaceutically acceptable carriers, provided that they are suitable for formulation and would not substantially affect the effect of pinocembrin crystalline form of the present invention.

One embodiment of the present invention relates to dosage forms comprising the pinocembrin crystalline forms solid. There are no limitations on specific dosage forms. For example, they can be tablets, capsules, pills, injections, sustained-release preparations, controlled-release preparations and the like.

One embodiment of the present invention provides use of the crystalline forms solid of pinocembrin, including α crystalline form, β crystalline form or the mixture of α crystalline form and β crystalline from in different proparations, for bringing about difference of drug uptake in treatment.

One embodiment of the present invention relates to the use of α crystalline form, β crystalline form, or the mixture of α crystalline form and β crystalline form of pinocembrin in different proportions in the manufacture of a medicament for treating diseases related to cerebral ischemia or a medicament for preventing diseases related to cerebral ischemia by protecting neurovascular unit function.

One embodiment of the present invention provides the use of pinocembrin for protecting neurovascular unit function in the treatment of diseases related to cerebral ischemia, and for improving the blood concentration in an organism due to the crystal form effect.

Morphologic Features of a Sample of α Crystalline Form of Pinocembrin According to an Embodiment:

For a sample of α crystalline form of pinocembrin obtained according to an embodiment of the present invention, when analyzed by X-ray single crystal diffraction, it showed monoclinic crystal system symmetry, the space group was $P2_1/c$, and the crystal cell parameter values were as follows: a=5.189 Å, b=24.149 Å, c=10.472 Å, α=90°, β=102.31° and γ=90°.

Figure 1:
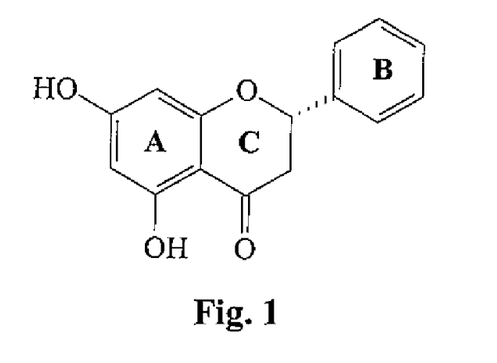
FIG. 1 is an illustration showing the relative configuration of the molecule.
Figure 2:
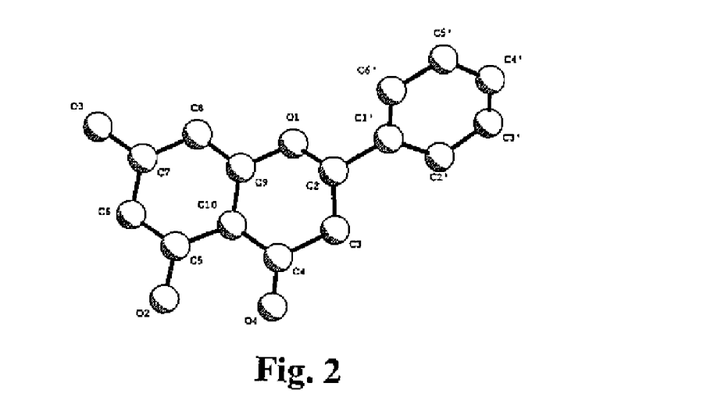
FIG. 2 is an illustration showing the stereo-structure projection of the molecule.
Figure 3:
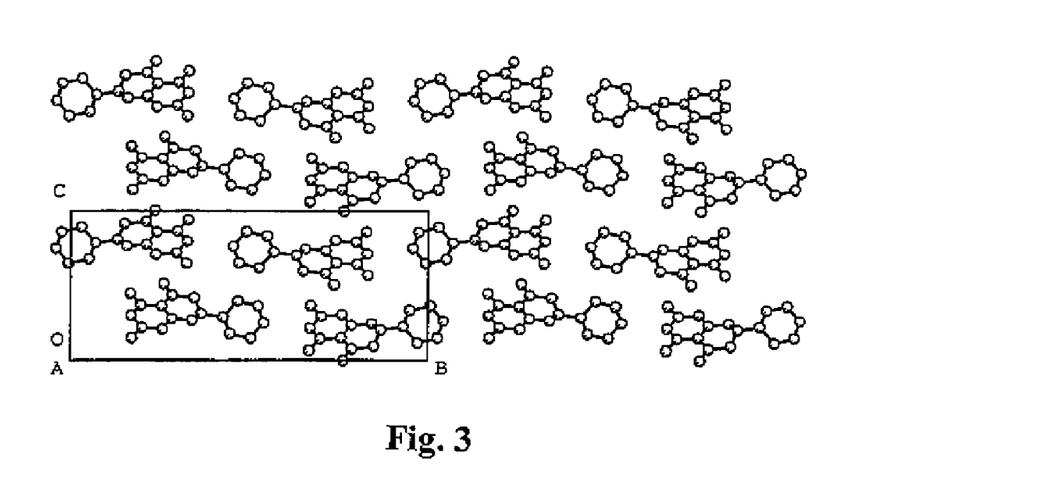
FIG. 3 is an illustration showing the unit cell stacking of the molecule (along the a axis).

FIG. 1 is an illustration showing the relative configuration of the molecule, FIG. 2 is an illustration showing the stereostructure projection of the molecule, FIG. 3 is an illustration showing the unit cell stacking of the molecule along the a axis. Table 1 shows atomic coordinate parameters and equivalent temperature factors. Table 2 shows bond length values of bonding atoms. Table 3 shows bond angle values of bonding atoms. As some carbon atoms of B ring adopt a disordered orientation state, the four atoms of $C_{2'}$, $C_{3'}$, $C_{5'}$, and $C_{6'}$ occupy two positions, with an occupancy rate of 0.5 respectively.

Formula 1 relative molecule configuration of α crystalline form of pinocembrin

TABLE 1

Atomic coordinate parameters (relative coordinate) of a sample of α crystalline form of pinocembrin

| | x | y | z | temperature factors | occupancy |
|---|---|---|---|---|---|
| O 1 | −.2023(8) | −.6574(2) | −.7376(4) | 3.4(2) | 1.0 |
| O 2 | −.4261(9) | −.8310(2) | −.5601(4) | 4.3(2) | 1.0 |
| O 3 | −.8660(9) | −.6732(2) | −.3557(4) | 4.2(2) | 1.0 |
| O 4 | −.6128(8) | −.7370(2) | −.4969(4) | 3.6(2) | 1.0 |
| C 2 | −.4094(24) | −.6318(3) | −.6954(12) | 3.5(8) | 1.0 |
| C 3 | −.5019(13) | −.6513(3) | −.5885(6) | 3.6(3) | 1.0 |
| C 4 | −.4859(12) | −.7131(3) | −.5720(6) | 3.0(3) | 1.0 |
| C10 | −.3269(12) | −.7427(2) | −.6435(6) | 2.8(3) | 1.0 |
| C 5 | −.2968(12) | −.8009(2) | −.6366(6) | 3.1(3) | 1.0 |
| C 6 | −.1407(13) | −.8289(2) | −.7054(6) | 3.3(3) | 1.0 |
| C 7 | −.0117(12) | −.7979(2) | −.7862(6) | 3.1(3) | 1.0 |
| C 8 | −.0336(12) | −.7405(2) | −.7966(6) | 2.8(3) | 1.0 |
| C 9 | −.1894(12) | −.7138(2) | −.7262(6) | 2.9(3) | 1.0 |
| C 1' | −.4049(18) | −.5701(3) | −.7176(9) | 6.7(5) | 1.0 |
| C 2' | −.316(5) | −.5292(7) | −.6099(19) | 7.4(2) | 0.5 |
| C 3' | −.326(5) | −.4730(7) | −.6436(21) | 7.4(1) | 0.5 |
| C 4' | −.3988(18) | −.4566(3) | −.7567(10) | 7.5(1) | 1.0 |
| C 5' | −.456(5) | −.4929(8) | −.8580(22) | 7.9(2) | 0.5 |
| C 6' | −.435(6) | −.5510(7) | −.8288(23) | 7.8(2) | 0.5 |
| C 2" | −.194(4) | −.5453(7) | −.6870(25) | 7.1(1) | 0.5 |
| C 3" | −.178(4) | −.4859(7) | −.700(3) | 7.3(2) | 0.5 |
| C 5" | −.630(4) | −.4859(7) | −.7856(22) | 7.4(1) | 0.5 |
| C 6" | −.640(4) | −.5432(6) | −.7752(22) | 8.8(1) | 0.5 |
| H 2 | −.591 | −.644 | −.779 | 7.6 | 1.0 |
| H 3A | −.701 | −.637 | −.587 | 5.0 | 1.0 |
| H 3B | −.369 | −.632 | −.502 | 5.0 | 1.0 |
| H 6 | −.116 | −.874 | −.697 | 4.3 | 1.0 |
| H 8 | .070 | −.717 | −.861 | 3.6 | 1.0 |
| HO 2 | −.525 | −.802 | −.507 | 3.2 | 1.0 |
| HO 3 | −.775 | −.699 | −.420 | 3.2 | 1.0 |
| H 2' | −.177 | −.548 | −.528 | 3.2 | 0.5 |
| H 3' | −.160 | −.447 | −.578 | 3.2 | 0.5 |
| H 4' | −.430 | −.413 | −.771 | 3.2 | 1.0 |
| H 5' | −.591 | −.477 | −.952 | 3.2 | 0.5 |
| H 6' | −.533 | −.577 | −.908 | 3.2 | 0.5 |
| H 2" | −.095 | −.557 | −.569 | 3.2 | 0.5 |
| H 3" | −.072 | −.456 | −.601 | 3.2 | 0.5 |
| H 5" | −.723 | −.469 | −.896 | 3.2 | 0.5 |
| H 6" | −.742 | −.570 | −.857 | 3.2 | 0.5 |

TABLE 2

Bond length values of bonding atoms of a sample of α crystalline form of pinocembrin (Å)

| Bonding Atoms | Bond Length | Bonding Atoms | Bond Length |
|---|---|---|---|
| O(1)—C(2) | 1.391(9) | C(6)—C(7) | 1.402(8) |
| O(1)—C(9) | 1.369(7) | C(6)—H(6) | 1.098(16) |
| O(2)—C(5) | 1.360(7) | C(7)—O(3) | 1.351(7) |
| O(2)—Ho(2) | 1.090(20) | C(7)—C(8) | 1.393(8) |
| O(3)—C(7) | 1.351(7) | C(8)—C(9) | 1.366(8) |
| O(3)—Ho(3) | 1.100(21) | C(8)—H(8) | 1.099(23) |
| O(4)—C(4) | 1.268(7) | C(1')—C(2') | 1.497(22) |
| C(2)—C(3) | 1.391(11) | C(1')—C(6') | 1.230(30) |
| C(2)—C(1') | 1.509(10) | C(2')—C(3') | 1.399(25) |
| C(2)—H(2) | 1.183(24) | C(2')—H(2') | 1.090(30) |
| C(3)—C(4) | 1.503(8) | C(3')—C(4') | 1.229(24) |
| C(3)—H(3A) | 1.087(21) | C(3')—H(3') | 1.160(30) |
| C(3)—H(3B) | 1.109(21) | C(4')—C(5') | 1.360(30) |
| C(4)—C(10) | 1.420(8) | C(4')—H(4') | 1.072(17) |
| C(10)—C(5) | 1.416(8) | C(5')—C(6') | 1.430(3) |
| C(10)—C(9) | 1.417(8) | C(5')—H(5') | 1.150(3) |
| C(5)—C(6) | 1.371(8) | C(6')—H(6') | 1.080(3) |

TABLE 3

Bond angle values of bonding atoms of a sample of α crystalline form of pinocembrin (°)

| Bonding atoms | Bond angle value | Bonding atoms | Bond angle value |
|---|---|---|---|
| C(2)—O(1)—C(9) | 116.2(5) | C(5)—C(6)—H(6) | 121.2(13) |
| C(5)—O(2)—Ho(2) | 107.8(11) | C(7)—C(6)—H(6) | 121.1(13) |
| C(7)—O(3)—Ho(3) | 113.3(11) | O(3)—C(7)—C(6) | 116.2(5) |
| C(4)—O(4)—Ho(2) | 102.1(9) | O(3)—C(7)—C(8) | 121.3(5) |
| C(4)—O(4)—Ho(3) | 117.2(8) | C(6)—C(7)—C(8) | 122.5(5) |
| O(1)—C(2)—C(3) | 121.9(7) | C(7)—C(8)—C(9) | 118.3(5) |
| O(1)—C(2)—C(1') | 110.5(6) | C(7)—C(8)—H(8) | 120.8(10) |
| O(1)—C(2)—H(2) | 101.5(12) | C(9)—C(8)—H(8) | 120.9(10) |
| C(3)—C(2)—C(1') | 118.5(7) | O(1)—C(9)—C(10) | 121.4(5) |
| C(3)—C(2)—H(2) | 99.1(13) | O(1)—C(9)—C(8) | 116.5(5) |
| C(1')—C(2)—H(2) | 99.8(11) | C(10)—C(9)—C(8) | 122.1(5) |
| C(2)—C(3)—C(4) | 114.0(6) | C(2)—C(1')—C(2') | 123.3(10) |
| C(2)—C(3)—H(3A) | 113.3(13) | C(2)—C(1')—C(6') | 120.9(11) |
| C(2)—C(3)—H(3B) | 104.8(14) | C(1')—C(2')—C(3') | 117.4(16) |
| C(4)—C(3)—H(3A) | 109.6(10) | C(1')—C(2')—H(2') | 111.2(16) |
| C(4)—C(3)—H(3B) | 107.7(10) | C(2')—C(3')—C(4') | 122.9(16) |
| H(3A)—C(3)—H(3B) | 106.9(15) | C(2')—C(3')—H(3') | 113.0(20) |
| O(4)—C(4)—C(3) | 120.1(5) | C(4')—C(3')—H(3') | 115.5(20) |
| O(4)—C(4)—C(10) | 122.2(5) | C(3')—C(4')—C(5') | 121.0(13) |
| C(3)—C(4)—C(10) | 117.6(5) | C(3')—C(4')—H(4') | 117.3(16) |
| C(4)—C(10)—C(5) | 123.0(5) | C(5')—C(4')—H(4') | 121.5(16) |
| C(4)—C(10)—C(9) | 120.0(5) | C(4')—C(5')—C(6') | 118.0(18) |
| C(5)—C(10)—C(9) | 117.0(5) | C(4')—C(5')—H(5') | 116.5(18) |
| O(2)—C(5)—C(10) | 119.8(5) | C(6')—C(5')—H(5') | 120.9(24) |
| O(2)—C(5)—C(6) | 117.9(5) | C(1')—C(6')—C(5') | 123.9(17) |
| C(10)—C(5)—C(6) | 122.3(5) | C(1')—C(6')—H(6') | 117.0(19) |
| C(5)—C(6)—C(7) | 117.8(5) | C(5')—C(6')—H(6') | 113.9(25) |

Note: in table 2 and 3, for the atoms $C_{2'}$, $C_{3'}$, $C_{5'}$ and $C_{6'}$ of B ring, only the bond length and bond angle values of one position are given in Table 2 and 3.

Figure 4:
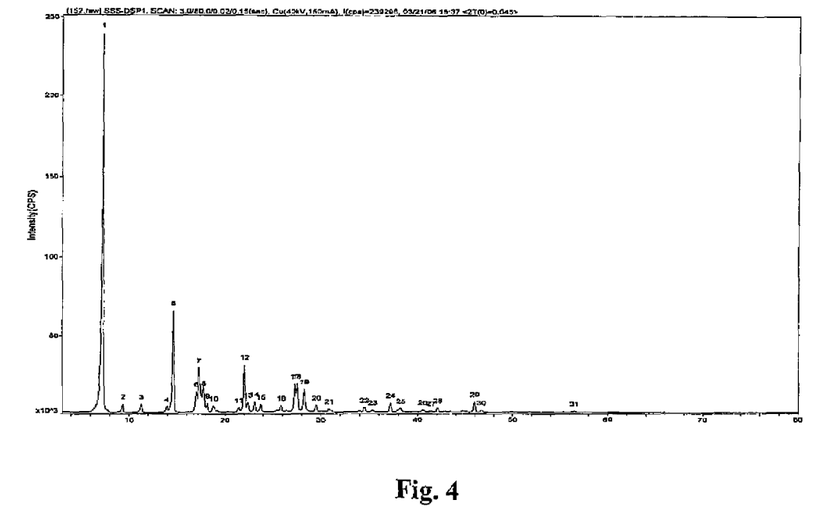
FIG. 4 is a powder X-ray diffraction pattern for a sample of α crystalline form of pinocembrin.

Powder (polycrystal) X-ray diffraction (CuK$_\alpha$ radiation) was performed on the α crystalline form solid of pinocembrin, and the diffraction peak locations: 2-Theta value (°) or d value (Å), and the relative strength of diffraction peak: peak height value (Height %) or peak area value (Area %) show the following characteristics (see Table 4, FIG. 4).

TABLE 4 characteristic peak values of powder X-ray diffraction for a sample of α crystalline form of pinocembrin

| Peak | 2-Theta | d(Å) | Height % | Area % |
|---|---|---|---|---|
| 1 | 7.32 | 12.07 | 100.0 | 100.0 |
| 2 | 9.37 | 9.44 | 2.3 | 2.5 |
| 3 | 11.30 | 7.82 | 2.1 | 2.2 |
| 4 | 13.93 | 6.35 | 1.5 | 2.5 |
| 5 | 14.65 | 6.04 | 27.3 | 27.1 |
| 6 | 17.04 | 5.20 | 5.5 | 8.7 |
| 7 | 17.31 | 5.12 | 11.8 | 18.2 |
| 8 | 17.80 | 4.98 | 5.6 | 26.6 |
| 9 | 18.16 | 4.88 | 2.2 | 1.8 |
| 10 | 18.83 | 4.71 | 1.6 | 2.1 |
| 11 | 21.47 | 4.13 | 0.9 | 0.5 |
| 12 | 22.06 | 4.03 | 12.5 | 13.8 |
| 13 | 22.40 | 3.97 | 2.2 | 2.4 |
| 14 | 23.09 | 3.85 | 2.6 | 2.0 |
| 15 | 23.74 | 3.74 | 1.8 | 1.6 |
| 16 | 25.83 | 3.45 | 1.5 | 1.8 |
| 17 | 27.30 | 3.26 | 7.2 | 9.6 |
| 18 | 27.51 | 3.24 | 7.1 | 14.1 |
| 19 | 28.29 | 3.15 | 5.7 | 6.4 |
| 20 | 29.53 | 3.02 | 1.7 | 1.9 |
| 21 | 30.88 | 2.89 | 0.8 | 1.0 |
| 22 | 34.51 | 2.60 | 1.2 | 1.2 |
| 23 | 35.37 | 2.54 | 0.5 | 0.6 |
| 24 | 37.21 | 2.41 | 2.4 | 2.4 |
| 25 | 38.27 | 2.35 | 0.8 | 1.4 |

TABLE 4-continued characteristic peak values of powder X-ray diffraction
for a sample of α crystalline form of pinocembrin

| Peak | 2-Theta | d(Å) | Height % | Area % |
|---|---|---|---|---|
| 26 | 40.53 | 2.22 | 0.5 | 0.8 |
| 27 | 41.40 | 2.18 | 0.3 | 0.3 |
| 28 | 42.09 | 2.15 | 1.1 | 1.1 |
| 29 | 45.96 | 1.97 | 2.8 | 3.2 |
| 30 | 46.67 | 1.94 | 0.5 | 0.7 |
| 31 | 56.49 | 1.63 | 0.3 | 0.5 |

Figure 5:
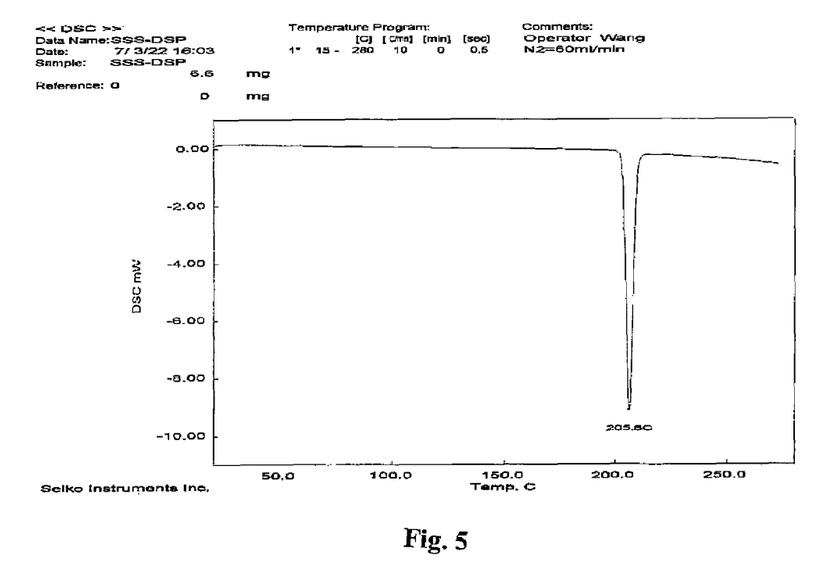
FIG. 5 is a DSC trace for a sample of α crystalline form of pinocembrin.

In an embodiment of the present invention, when analyzed by DSC, α crystalline form solid of pinocembrin shows a decalescence transition temperature of about 206° C. (see FIG. 5).

Figure 6:
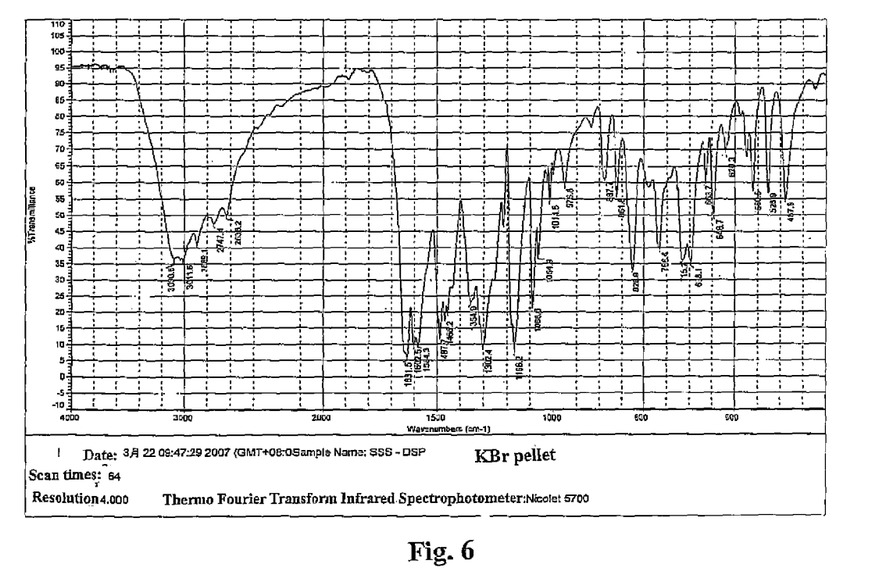
FIG. 6 is an infrared absorption spectra for a sample of α crystalline form of pinocembrin.

IR analysis with KBr pellet was performed on α crystalline form solid of pinocembrin (see FIG. 6).The characteristic peaks were as follows: 3090.6, 3011.6, 2889.1, 2747.4, 2636.2, 1631.5, 1602.5, 1584.3, 1487.7, 1466.2, 1454.5, 1435.6, 1354.9, 1302.4, 1257.0, 1217.0, 1168.2, 1088.6, 1064.9, 1028.0, 1014.6, 1001.3, 975.8, 918.0, 887.7, 861.8, 825.9, 789.9, 766.4, 715.2, 698.1, 663.7, 646.7, 620.3, 587.3, 574.9, 560.5, 526.9 and 487.9 $cm^{-1}$, wherein the peaks of 2891.1, 2747.4, 2636.2, 1631.5 and 1354.9 $cm^{-1}$ were the main characteristic peaks of α crystalline form solid of pinocembrin.

Figure 7:
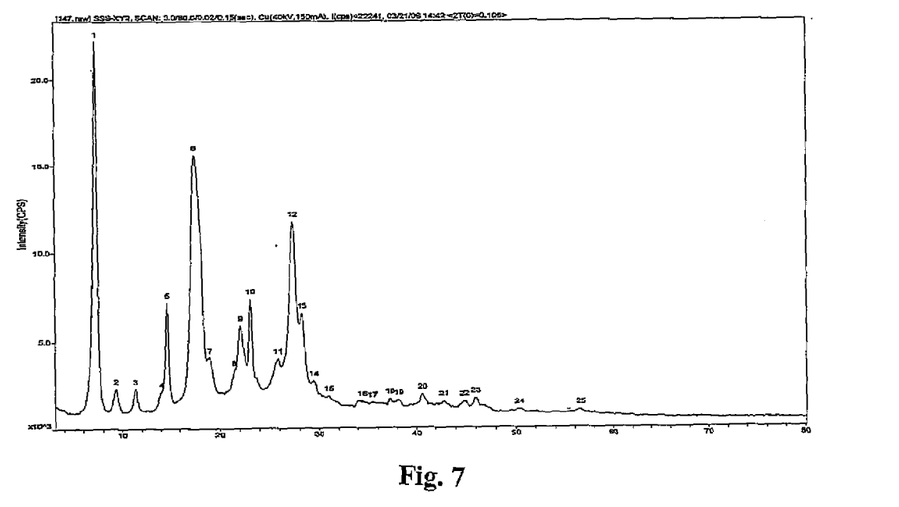
FIG. 7 is a powder X-ray diffraction pattern for a sample of β crystalline form of pinocembrin.

Morphologic Features of a Sample of β Crystalline Form of Pinocembrin According to an Embodiment:

For β crystalline form of pinocembrin obtained according to an embodiment of the present invention, when analyzed by powder (polycrystal) X-ray diffraction ($CuK_\alpha$ radiation), it showed the diffraction peak location:2-Theta value (°) or d value (Å) and the relative strength of diffraction peak: peak height value (Height %) or peak area value (Area %), shown as the following characteristic peak values (see Table 5, FIG. 7)

TABLE 5 characteristic peak values of powder X-ray diffraction
for a sample of β crystalline form of pinocembrin

| Peak | 2-Theta | d(Å) | Height % | Area % |
|---|---|---|---|---|
| 1 | 7.33 | 12.06 | 100.0 | 66.5 |
| 2 | 9.41 | 9.40 | 6.2 | 4.9 |
| 3 | 11.33 | 7.81 | 6.1 | 4.5 |
| 4 | 14.07 | 6.29 | 2.9 | 2.2 |
| 5 | 14.69 | 6.03 | 27.2 | 17.6 |
| 6 | 17.49 | 5.07 | 63.9 | 100.0 |
| 7 | 19.01 | 4.67 | 2.8 | 1.5 |
| 8 | 21.49 | 4.13 | 0.1 | 0 |
| 9 | 22.11 | 4.02 | 12.9 | 11.2 |
| 10 | 23.17 | 3.84 | 19.4 | 9.5 |
| 11 | 25.91 | 3.44 | 3.3 | 2.5 |
| 12 | 27.41 | 3.25 | 31.7 | 27.4 |
| 13 | 28.31 | 3.15 | 19.0 | 15.1 |
| 14 | 29.51 | 3.02 | 1.6 | 0.3 |
| 15 | 31.03 | 2.88 | 0.7 | 0.4 |
| 16 | 34.47 | 2.60 | 1.0 | 1.5 |
| 17 | 35.45 | 2.53 | 0.4 | 0.2 |
| 18 | 37.24 | 2.41 | 1.5 | 0.7 |
| 19 | 38.15 | 2.36 | 1.2 | 0.9 |
| 20 | 40.61 | 2.22 | 3.1 | 2.8 |
| 21 | 42.83 | 2.11 | 1.5 | 1.4 |
| 22 | 44.89 | 2.02 | 1.6 | 1.3 |
| 23 | 46.01 | 1.97 | 2.4 | 1.8 |
| 24 | 50.36 | 1.81 | 0.7 | 0.8 |
| 25 | 56.63 | 1.62 | 1.0 | 0.9 |

Figure 8:
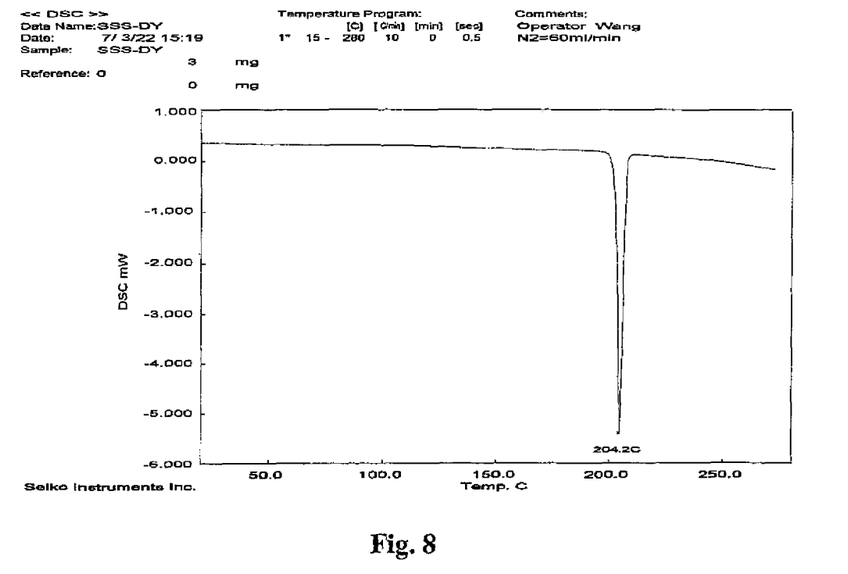
FIG. 8 is a DSC trace for a sample of β crystalline form of pinocembrin.

In an embodiment of the present invention, when analyzed by DSC, β crystalline form solid of pinocembrin shows a decalescence transition temperature of about 204° C. (see FIG. 8).

Figure 9:
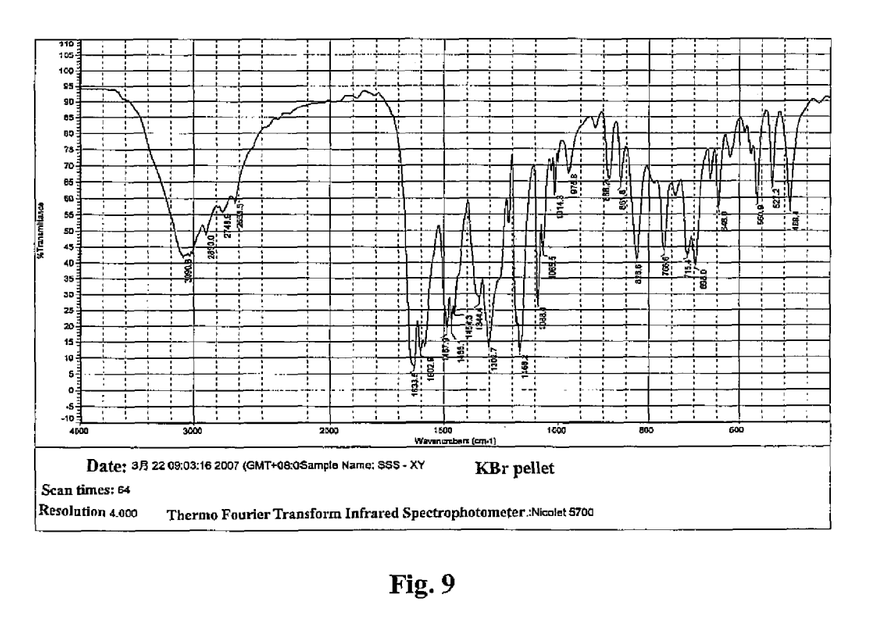
FIG. 9 is an infrared absorption spectra for a sample of β crystalline form of pinocembrin.

IR analysis with KBr pellet was performed on β crystalline form solid of pinocembrin according to an embodiment of the present invention (see FIG. 9). The characteristic peaks were as follows: 3090.8, 2890.0, 2748.9, 2638.3, 1633.5, 1602.9, 1585.0, 1487.9, 1466.1, 1454.3, 1344.4, 1302.7, 1216.7, 1168.2, 1088.4, 1065.5, 1028.8, 1014.3, 1001.5, 975.8, 917.8, 888.2, 861.8, 826.6, 789.1, 766.6, 741.1, 715.4, 698.0, 663.7, 646.0, 620.5, 587.9, 574.8, 560.9, 527.2 and 488.4 $cm^{-1}$, wherein the peaks of 2890.0. 2748.9. 2638.3, 1633.5 and 1344.4 $cm^{-1}$ were the main characteristic peaks of β crystalline form solid of pinocembrin.

Method for Preparing a Sample of α Crystalline Form of Pinocembrin According to an Embodiment of the Present Invention (1) dissolving a sample completely in a solvent selected from the group consisting of methanol, ethanol, chloroform, acetone, ethyl acetate, n-butanol, isopropanol, acetonitrile, THF, dioxane, 95% ethanol, glacial acetic acid, formic acid, ether, dichloromethane, toluene, benzene, n-hexane, cyclohexane, dioxane, DMF, petroleum ether, ammonia, n-propanol, or a mixture thereof, then, (a) placing the mixture in a condition of temperature 4-50° C. and relative humidity 10%-75% to allow recrystallization for 1 to 60 days, or (b) adding water to allow precipitate, then obtaining α crystalline form of pinocembrin through filtration under reduced pressure, freeze-drying or cold spray.

Method for Preparing a Sample of β Crystalline Form of Pinocembrin According to an Embodiment of the Present Invention using a sample of α crystal form solid as the material, then obtaining a sample of β crystalline form of pinocembrin through (a) crystal transition by grinding, or (b) dissolving the material completely in a solvent of pyridine or DMSO, adding water to allow precipitate, and performing filtration under reduced pressure, freeze-drying or cold spray.

Pharmacodynamics Characteristics of Pinocembrin Sample:

Pure α crystalline form, pure β crystalline form or the mixture of α and β crystalline forms of pinocembrin in any proportion according to the present invention have an effect on treating diseases related to cerebral ischemia or preventing diseases related to cerebral ischemia by protecting neurovascular unit function.

There is a difference in bioavailability between pure α crystalline form and pure β crystalline form of present invention. For oral administration, the bioavailability of β crystalline form is more than 2 times higher than that of α crystalline form. For a mixture of the two crystalline forms in any proportion, the bioavailability thereof can vary, dependent on different contents of β crystalline form.

Dosage and Preparation Characteristics:

For a pharmaceutical composition or a preparation comprising pure α crystalline form, pure β crystalline form or a mixture thereof in any proportion of pinocembrin according to an embodiment of present invention, daily dosage is 5~250 mg, based on pinocembrin crystalline forms solid. Preparations include tablets, capsules, pills, injections, sustained-release preparations, controlled-release preparations and the like.

DETAILED DESCRIPTION OF THE INVENTION

The following exemplary examples are provided for the purpose of better description of the present invention, however, it should be appreciated that the present invention is not limited to the given examples.

Instruments and Test Conditions for the Following Examples:
1. Monocrystal X-ray analysis
   Instrument: MAC DIP-2030K area detector
   Test condition: tube voltage: 50 KV, tube flow: 80 mA, ω scanning, $MoK_\alpha$, $2\theta \leq 50.0°$, scan range: 0-180°, pivot angle: 6°, step: 6°, scan rate: 1.8°/min.
2. Powder X-ray analysis
   Instrument: Rigaku D/max 2550 powder X-ray diffractometer
   Test conditions: voltage: 40 KV, current: 150 mA, scan rate: 8°/min.
3. DSC analysis
   Instrument type: Seiko Instruments Inc. Differential Scanning Calorimeter
   Test conditions: purge gas: $N_2$, heating rate: 10° C./min. Temperature range: 25-250° C.
4. IR absorbance spectra
   Instrument Nicolet FT-IR spectrometer: IMPACT 400
   Test conditions: KBr pellet
5. HPCL analysis
   Instrument: SHIMADZU LC-10Avp high performance liquid chromatography, SPD-M10Avp diode array detector, CLASS-VP chromatography data system; column: Alltch $C_{18}$(5μ, 150×4.6 mm); test conditions: column temperature: room temperature; wavelength: 290 nm; mobile phase: methanol/phosphate saline pH 3.0 (64/36); flow rate : 1.0 mL/min; injection volume: 20 μL; injection concentration: 500.0 μg/mL Preparation 1: Synthesis of Pinocembrin Sample To 1000 ml hydrogenation reaction kettle, was added 5 g (19.7 mmol) of 5,7-dihydroxyflavone, 650 ml of anhydrous ethanol, and 1.5 g of 10% palladium on carbon. Under a hydrogen pressure of 0.13 Mpa, the reaction was performed for 4 h at 40° C. When the reaction was finished, the palladium on carbon was filtered. The filtrate was concentrated, then separated and purified by column chromatography (eluted by methanol:acetic ether:petroleum ether=2:10:100 (V:V:V)) under vacuum. The solvent was evaporated to dryness, and 3.9 g of white amorphous solid powder was obtained (purity: 98.6%, detected by HPLC) in a yield of 52%[2].

Preparation of a Sample of α Crystalline Form of Pinocembrin

EXAMPLE 1

Method 1 for Preparing a Sample of α Crystalline Form of Pinocembrin 5 g pinocembrin sample was added to 20 ml of 95% ethanol, and was heated to be dissolved completely, then cooled to room temperature and allowed to stand for 24 h. White solid was precipitated, and was filtered and dried. 4.5 g of white crystalline (purity: 98.8%, detected by HPLC) was obtained in a recovery of 90%.

The obtained crystalline was analyzed by X-ray single crystal diffraction. It showed monoclinic symmetry, space group was $P2_1/c$, and the crystal cell parameter values were a=5.189 Å, b=24.149 Å, c=10.472 Å, α=90°, β=102.31° and γ=90°.

Powder (polycrystal) X-ray diffraction ($CuK_\alpha$ radiation) was performed on the obtained crystalline. The characteristic peak values of the diffraction peak location: 2-Theta value (°) or d value (Å) and the relative strength of diffraction peak: peak height value (Height %) or peak area value (Area %) were shown in Table 4, and the obtained trace was shown in FIG. 4.

DSC analysis was performed on the obtained crystalline, and decalescence transition temperature was 206° C.

IR analysis with KBr pellet was performed on the crystalline obtained, and the characteristic peaks were as follows: 3090.6, 3011.6, 2889.1, 2747.4, 2636.2, 1631.5, 1602.5, 1584.3, 1487.7, 1466.2, 1454.5, 1435.6, 1354.9, 1302.4, 1257.0, 1217.0, 1168.2, 1088.6, 1064.9, 1028.0, 1014.6, 1001.3, 975.8, 918.0, 887.7, 861.8, 825.9, 789.9, 766.4, 715.2, 698.1, 663.7, 646.7, 620.3, 587.3, 574.9, 560.5, 526.9 and 487.9 cm$^{-1}$.

The above spectra data showed that the crystalline form obtained in the present example was α crystalline form.

EXAMPLES 2 TO 10

Methods 2 to 10 for Preparing a Sample of α Crystalline Form of Pinocembrin

Referring to the preparation method of Example 1, using ethyl acetate, chloroform, acetone, acetonitrile, THF, ether, benzene, cyclohexane or DMF as the solvent, white crystalline of pinocembrin was obtained. The results of the experiments were shown in table 6. Powder X-ray diffraction, DSC and IR analysis were performed on the obtained crystalline, and the results showed that the crystalline form was α crystalline form of pinocembrin.

TABLE 6

Results of the preparation of samples of α crystalline form of pinocembrin

| example | reaction solvent | product weight (g) | HPLC purity (%) | recovery (%) |
|---|---|---|---|---|
| 2 | ethyl acetate | 4.40 | 99.0 | 88 |
| 3 | chloroform | 4.30 | 98.7 | 86 |
| 4 | acetone | 4.30 | 99.1 | 86 |
| 5 | acetonitrile | 4.20 | 98.9 | 84 |
| 6 | THF | 4.25 | 98.8 | 85 |
| 7 | ether | 4.35 | 98.6 | 87 |
| 8 | benzene | 4.20 | 98.9 | 84 |
| 9 | cyclohexane | 4.20 | 98.6 | 84 |
| 10 | DMF | 4.20 | 98.7 | 84 |

EXAMPLE 11

Method 11 for Preparing the Sample of α Crystalline Form of Pinocembrin 5 g pinocembrin sample was dissovled in 100 ml mixture of 95% ethanol and acetone (95% ethanol:acetone=1:1) completely at room temperature, then 100 ml water was added under stirring, and white precipitate appeared. The precipitate was filtered under reduced pressure and dried to obtain 4.00 g white crystalline (purity: 98.7%) in a recovery of 80.0%. Powder X-ray diffraction, DSC and IR analysis were performed on the obtained crystalline form, and the results showed that the crystalline form obtained was α crystalline form of pinocembrin.

EXAMPLES 12 TO 16

Methods 12 to 16 for Preparing a Sample of α Crystalline Form of Pinocembrin Referring to the preparation method of Example 1, using the mixture of isopropanol and THF (isopropanol:THF=2:1), the mixture of acetonitrile and DMF (acetonitrile:DMF=4:1), the mixture of methanol and acetone (methanol:acetone=3:2), the mixture of ethanol and acetonitrile (ethanol:acetonitrile=1:1), and the mixture of ethanol, acetone and glacial acetic acid (ethanol:acetone:glacial acetic acid=2:1:0.1) as the solvents, white crystalline of pinocembrin was obtained. The results of the experiments were shown in Table 7. Powder X-ray diffraction, DSC and IR analysis were performed on the obtained crystalline, and the results showed that the crystalline form obtained was α crystalline form of pinocembrin.

TABLE 7

Results of samples of α crystalline form of pinocembrin

| example | reaction solvent | product weight (g) | HPLC purity (%) | recovery (%) |
|---|---|---|---|---|
| 12 | 2:1 isopropanol-THF | 4.00 | 98.8 | 80 |
| 13 | 4:1 acetonitrile-DMF | 3.80 | 98.7 | 76 |
| 14 | 3:2 methanol-acetone | 3.90 | 98.9 | 78 |
| 15 | 1:1 ethanol-acetonitrile | 4.05 | 99.0 | 81 |
| 16 | 2:1:0.1 ethanol-acetone-glacial acetic acid | 4.10 | 98.9 | 82 |

Preparation of a Sample of β Crystalline Form of Pinocembrin

EXAMPLE 17

Method 1 for Preparing a Sample of β Crystalline Form of Pinocembrin:

10 g sample of α crystalline form of pinocembrin was placed in a mortar, grinded evenly in the same direction for 1 hour at room temperature, and white crystalline was obtained, which is different from α crystalline form.

Powder (polycrystal) X-ray diffraction (CuK$_\alpha$ radiation) was performed on the obtained crystalline. The characteristic peak values of the diffraction peak location:2-Theta value (°) or d value (Å) and the relative strength of diffraction peak: peak height value (Height %) or peak area value (Area %), were shown in Table 5, and the obtained trace was shown in FIG. 7.

DSC analysis was performed on the obtained crystalline, and decalescence transition temperature was 204° C., as showed in the DSC trace.

IR analysis with KBr pellet was performed on the crystalline obtained, and the characteristic peaks were as follows: 3090.8, 2890.0, 2748.9, 2638.3, 1633.5, 1602.9, 1585.0, 1487.9, 1466.1, 1454.3, 1344.4, 1302.7, 1216.7, 1168.2, 1088.4, 1065.5, 1028.8, 1014.3, 1001.5, 975.8, 917.8, 888.2, 861.8, 826.6, 789.1, 766.6, 741.1, 715.4, 698.0, 663.7, 646.0, 620.5, 587.9, 574.8, 560.9, 527.2 and 488.4 cm$^{-1}$.

The above spectra date showed that the crystalline form obtained in the present example was β crystalline form.

EXAMPLE 18

Method 2 for Preparing β Crystalline Form of Pinocembrin

At room temperature, 5 g pinocembrin sample was dissolved in 75 ml DMSO, then to which 150 ml of water was added under stirring, and white precipitate appeared. The precipitate was filtered and dried to obtain 4.2 g white crystalline (purity: 98.8%, detected by HPLC) in a recovery of 84.0%. Powder X-ray diffraction, DSC and IR analysis were performed on the obtained crystalline, and the results showed that the crystalline form obtained was β crystalline form of pinocembrin.

EXAMPLE 19

Method 3 for Preparing a Sample of β Crystalline Form of Pinocembrin

Except that pyridine was used as the solvent, the same preparation method as that of Example 18 was used, and 8.8 g white crystalline was obtained (purity: 98.6%, detected by HPLC) in a recovery of 88.0%. Powder X-ray diffraction, DSC and IR analysis were performed on the obtained crystalline, and the results showed that the crystalline form obtained was β crystalline form of pinocembrin.

EXAMPLE 20

Method for Preparing a Sample of Pinocembrin Mixture of α Crystalline Form and β crystalline form in a ratio 1:1

10 g of pinocembrin sample α and β crystalline form were respectively weighed and placed into a sealable vessel. The vessel was sealed and shook to mix the solid evenly. The mixture sample of α and β crystalline form in a ratio 1:1 was obtained.

Formulation

EXAMPLE 21

Method 1 for Preparing a Combined Pharmaceutical Preparation (Tablet)

The samples of pure α crystalline form, pure β crystalline form, or solid mixture of (α+β) crystalline form (α:β=1:1) of pinocembrin were mixed with excipients in different proportions to obtain a solid of the combined pharmaceutical active ingredients. Tablets containing 5~60 mg of active ingredients were prepared. The tablet formula were given in Table 8.

TABLE 8

Preparation formula for combined pinocembrin tablets

| components | amount (g/1000 tablets) | | | | | | |
|---|---|---|---|---|---|---|---|
| | Formula 1 | Formula 2 | Formula 3 | Formula 4 | Formula 5 | Formula 6 | Formula 7 |
| Pinocembrin (g) | 5.0 | 10.0 | 20.0 | 30.0 | 40.0 | 50.0 | 60.0 |
| Lactose (g) | 100.0 | 100.0 | 100.0 | 100.0 | 100.0 | 100.0 | 100.0 |
| Starch (g) | 35 | 30 | 20 | 10 | — | — | — |
| Low-substituted hydroxypropyl cellulose (g) | 3.0 | 3.0 | 3.0 | 3.0 | 3.0 | 3.0 | 3.0 |
| MCC (g) | — | — | — | — | 3.0 | 3.0 | 3.0 |
| Talc powder (g) | 6.0 | 6.0 | 6.0 | 6.0 | 6.0 | 6.0 | 6.0 |
| Magnesium stearate (g) | 1.0 | 1.0 | 1.0 | 1.0 | 1.0 | 1.0 | 1.0 |
| 1% Sodium hydroxymethyl cellulose | q.s. | q.s. | q.s. | q.s. | q.s. | q.s. | q.s. |

The detailed preparation method was as follows: mixing the excipients with pinocembrin evenly, then adding appropriate amount of 1% sodium hydroxymethyl cellulose solution to make a dough. The dough was screened to obtain granules. The wet granules were dried and sieved. Then magnesium stearate and talc powder were added and mixed evenly, and the product was obtained by tabletting.

EXAMPLE 22

Method 2 for Preparing a Combined Pharmaceutical Formulation (Capsule)

The samples of pure α crystalline form, pure β crystalline form, or solid mixture of (α+β) crystalline form (α:β=1:1 or 1:3) of pinocembrin were mixed with excipients in different proportions to obtain a solid of the combined pharmaceutical active ingredients. The capsules containing 5~60 mg of active ingredients were prepared. The capsule formulas were given in Table 9.

The detailed preparation method was as follows: mixing the excipients with pinocembrin evenly, then appropriate amount of 1% sodium hydroxymethyl cellulose solution was added to make wet granules, the wet granules were dried and sieved. Then magnesium stearate was added and mixed evenly, and the product was obtained by filling the mixture above into empty capsules. Alternatively, without granulation, the product was obtained by filling the excipients and pinocembrin into empty capsules directly, after they were mixed evenly and sieved.

EXAMPLE 23

Method 3 for Preparing Combined Pharmaceutical Formulation (Injection Solution and Freeze-dried Powder for Injection)

Pure α crystalline form, pure β crystalline form, or solid mixture of (α+β) crystalline form (α:β=1:1) of pinocembrin were mixed with excipients in different proportions to obtain a solid of the combined pharmaceutical active ingredients.

TABLE 9

Preparation formulas for combined pinocembrin capsules

| components | Amount (g/1000 capsules) | | | | | | |
|---|---|---|---|---|---|---|---|
| | Formula 1 | Formula 2 | Formula 3 | Formula 4 | Formula 5 | Formula 6 | Formula 7 |
| Pinocembrin (g) | 5.0 | 10.0 | 20.0 | 30.0 | 40.0 | 50.0 | 60.0 |
| Lactose (g) | — | — | — | — | — | — | — |
| Starch (g) | 100.0 | 100.0 | 100.0 | 100.0 | — | — | — |
| MCC (g) | — | — | — | — | 70.0 | 60.0 | 50.0 |
| Magnesium stearate (g) | 1.0 | 1.0 | 1.0 | 1.0 | 1.0 | 1.0 | 1.0 |
| 1% Sodium hydroxymethyl cellulose | q.s. | q.s. | q.s. | q.s. | q.s. | q.s. | q.s. |

Then the injections containing 5~60 mg of active ingredients per ampoule were obtained. The injection formulas were given in Table 10.

TABLE 10

Preparation formula for combined pinocembrin injections

| components | Formula 1 | Formula 2 | Formula 3 | Formula 4 |
|---|---|---|---|---|
| Pinocembrin (g) | 1 | 1 | 1 | 1 |
| Hydroxypropyl-β-cyclodextrin (g) | 40 | 40 | 20 | 20 |
| Distilled water (ml) | 400 | 100 | 10000 | 10000 |
| Ethanol (ml) | 20 | 20 | 20 | 20 |
| Sodium chloride (g) | | | 90 | |
| Dextrose (g) | | | | 500 |

Formula 1: Preparation of Pinocembrin Injection Solution (1) To 400 ml of distilled water, 40 g of hydroxypropyl-β-cyclodextrin was added and dissolved with stirring;

(2) To 20 ml ethanol, 1 g of pinocembrin was added and dissolved, then the obtained solution was added into the hydroxypropyl-β-cyclodextrin solution mentioned above;

(3) The mixed solution was stirred magnetically for 20 min at 40~50° C. When the solution became clear and transparent, 0.5 g of actived carbon for injection was added. Then the mixture was heated to 80° C. with stirring and kept at this temperature for 15 min, then the carbon was filtered. The filtrate was subpackaged into ampoule at 4 ml each. Pinocembrin injection solution was obtained after sterilizing at 121° C. for 15 min.

Formula 2: Preparation of Pinocembrin Freeze-dried Powder for Injection (1) In the sterile room, 40 g of hydroxypropyl-β-cyclodextrin was weighed and dissolved in water to make 150 ml solution. 0.1 g actived carbon was added, and the mixture was heated to mild boiling for 15 min, and then the carbon was filtered out;

(2) 1 g of pinocembrin was dissolved in 20 ml anhydrous ethanol, then the obtained solution was added into the hydroxypropyl-β-cyclodextrin solution mentioned above;

(3) The mixture was stirred magnetically for 20 min at 40~50° C.- When the solution became clear and transparent, the inclusion complex solution of pinocembrin in hydroxypropyl-β-cyclodextrin was obtained;

(4) Water was added to the inclusion complex solution to 200 ml. The mixture was filtered through 0.22 μm filter membrane. The filtrate was subpackaged into vial of 10 ml (2 ml/vial), and placed into freeze dryer to freeze-dry. The sterile powder for injection was obtained after the vials' stoppers were sealed.

Formula 3: Preparation of Pinocembrin Sodium Chloride Infusion (1) To 200 ml of distilled water, 20 g of hydroxypropyl-β-cyclodextrin was added and dissolved with stirring. 0.5 g actived carbon for infusion was added. The mixture was heated to 80° C. with stirring and kept at this temperature for 15 min, then the carbon was filtered;

(2) 1 g of pinocembrin was weighed and dissolved in 20 ml anhydrous ethanol, then the obtained solution was poured into the hydroxypropyl-β-cyclodextrin solution mentioned above;

(3) The mixture was stirred magnetically for 20 min at 40~50° C. When the solution became clear and transparent, the inclusion complex solution of pinocembrin in hydroxypropyl-β-cyclodextrin was obtained;

(4) Water was added to the inclusion complex solution to 800 ml. After adding 90 g sodium chloride for injection, the solution was adjusted to a pH of 8~9 and diluted to 10000 ml with water. Then 10 g actived carbon for injection was added, and stirred for 20 min;

(5) After the carbon was removed, the solution was subpackaged in 100 ml per bottle. The product was obtained after sterilizing at 121° C. for 30 min.

Formula 4: Preparation of Pinocembrin Dextrose Infusion (1) 20 g of hydroxypropyl-β-cyclodextrin was added to 200 ml of distilled water and dissolved with stirring. 0.5 g actived carbon for infusion was added. The mixture was heated to 80° C. by stirring and kept at this temperature for 15 min, then the carbon was filtered;

(2) 1 g of pinocembrin was dissolved in 20 ml anhydrous ethanol, then the obtained solution was poured into the hydroxypropyl-β-cyclodextrin solution mentioned above;

(3) The mixture was stirred magnetically for 20 min at 40~50° C. When the solution became clear and transparent, the inclusion complex solution of pinocembrin in hydroxypropyl-β-cyclodextrin was obtained;

(4) Water was added to the inclusion complex solution to 800 ml. After adding 500 g glucose for injection, the solution was adjusted to a pH of 8~9 and diluted to 10000 ml with water. Then 10 g actived carbon for injection was added, and stirred for 20 min;

(5) After the carbon was removed, the solution was subpackaged in 100 ml per bottle. The product was obtained after sterilizing at 121° C. for 30 min.

EXAMPLE 24

In vivo Absorption and Blood Concentration Characteristics for Pinocembrin Solid Active Ingredient of α and β Crystalline Forms:

18 of SD rats, female and male each half, with body weight of 230~250 g, were randomized into 3 groups, with 6 rats each group and female half. After 10 hours of fasting but free water intake, the rats were administrated with pinocembrin solid active ingredient powder of α, β or 1:1 (α+β) mixed crystalline forms, at a dose of 50 mg/kg to stomach. Then the arterial blood samples at different times were taken and the contents of pinocembrin were determined. The result showed that for pinocembrin of different crystalline forms, at the same dosage by oral administration, the blood concentrations and the time to reach the peak concentration were different, wherein the blood concentration of α crystalline form was obviously lower than that of β crystalline form.

TABLE 11

Blood concentrations at different time for rats having been administered orally with pinocembrin samples of different crystalline forms (detected by HPLC, peak area value)

| | time | | | |
|---|---|---|---|---|
| crystalline forms | 10 min | 20 min | 30 min | 40 min |
| β crystalline from | 13.2 | 48.6 | 14.6 | 14.2 |
| 1:1 (α + β) crystalline forms | 8.5 | 15.6 | 7.9 | 7.1 |
| α crystalline form | 3.8 | 9.7 | 4.4 | 3.5 |

Note:
the blood concentrations listed in the table were the average for the rats in each group.

REFERENCES

1. Chinese patent: publication number CN1695608A
2. ChengYonghao, etc. synthesis of 5,7-dihydricflavanone, chemical reagents, 2006, 28(7): 437

What is claimed is:

1. β crystalline form of pinocembrin of formula (I):

(I)

characterized in that, when analyzed by X-ray powder (polycrystal) diffraction (CuK$_\alpha$ radiation), the diffraction peak locations: 2-Theta value)(°) or d value (Å), and the relative strength of diffraction peak: peak height value (Height %) or peak area value (Area %), show the following characteristics:

| Peak | 2-Theta | d(Å) | Height % | Area % |
|---|---|---|---|---|
| 1 | 7.33 | 12.06 | 100.0 | 66.5 |
| 2 | 9.41 | 9.40 | 6.2 | 4.9 |
| 3 | 11.33 | 7.81 | 6.1 | 4.5 |
| 4 | 14.07 | 6.29 | 2.9 | 2.2 |
| 5 | 14.69 | 6.03 | 27.2 | 17.6 |
| 6 | 17.49 | 5.07 | 63.9 | 100.0 |
| 7 | 19.01 | 4.67 | 2.8 | 1.5 |
| 8 | 21.49 | 4.13 | 0.1 | 0 |
| 9 | 22.11 | 4.02 | 12.9 | 11.2 |
| 10 | 23.17 | 3.84 | 19.4 | 9.5 |
| 11 | 25.91 | 3.44 | 3.3 | 2.5 |
| 12 | 27.41 | 3.25 | 31.7 | 27.4 |
| 13 | 28.31 | 3.15 | 19.0 | 15.1 |
| 14 | 29.51 | 3.02 | 1.6 | 0.3 |
| 15 | 31.03 | 2.88 | 0.7 | 0.4 |
| 16 | 34.47 | 2.60 | 1.0 | 1.5 |
| 17 | 35.45 | 2.53 | 0.4 | 0.2 |
| 18 | 37.24 | 2.41 | 1.5 | 0.7 |
| 19 | 38.15 | 2.36 | 1.2 | 0.9 |
| 20 | 40.61 | 2.22 | 3.1 | 2.8 |
| 21 | 42.83 | 2.11 | 1.5 | 1.4 |
| 22 | 44.89 | 2.02 | 1.6 | 1.3 |
| 23 | 46.01 | 1.97 | 2.4 | 1.8 |
| 24 | 50.36 | 1.81 | 0.7 | 0.8 |
| 25 | 56.63 | 1.62 | 1.0 | 0.9. |

2. The β crystalline form of pinocembrin according to claim 1, characterized in that, the decalescence transition temperature of DSC trace is about 204° C.

3. The β crystalline form of pinocembrin according to claim 1, characterized in that, the infrared absorption spectra thereof shows the following peaks: 3090.8, 2890.0, 2748.9, 2638.3, 1633.5, 1602.9, 1585.0, 1487.9, 1466.1, 1454.3, 1344.4, 1302.7, 1216.7, 1168.2, 1088.4, 1065.5, 1028.8, 1014.3, 1001.5, 975.8, 917.8, 888.2, 861.8, 826.6, 789.1, 766.6, 741.1, 715.4, 698.0, 663.7, 646.0, 620.5, 587.9, 574.8, 560.9, 527.2 and 488.4 cm$^{-1}$, wherein the peaks 2890.0, 2748.9, 2638.3, 1633.5 and 1344.4 cm$^{-1}$ are the main characteristic peaks of the β crystalline form of pinocembrin.

4. A mixed crystalline form of pinocembrin consisting of α crystalline form and β crystalline form of pinocembrin in any proportion,
wherein
when the α crystalline form is analyzed by X-ray single crystal diffraction, it shows monoclinic crystal system symmetry, the space group is P2$_1$/c, and the crystal cell parameter values are as follows: a=5.189Å, b=24.149Å, c=10.472Å, α=90°, β=102.31° and γ=90°, or
when the α crystalline form is analyzed by X-ray powder (polycrystal) diffraction (CuK$_\alpha$ radiation), the diffraction peak locations: 2-Theta value)(°) or d value (Å), and the relative strength of diffraction peak: peak height value (Height %) or peak area value (Area %) show the following characteristics:

| Peak | 2-Theta | d(Å) | Height % | Area % |
|---|---|---|---|---|
| 1 | 7.32 | 12.07 | 100.0 | 100.0 |
| 2 | 9.37 | 9.44 | 2.3 | 2.5 |
| 3 | 11.30 | 7.82 | 2.1 | 2.2 |
| 4 | 13.93 | 6.35 | 1.5 | 2.5 |
| 5 | 14.65 | 6.04 | 27.3 | 27.1 |
| 6 | 17.04 | 5.20 | 5.5 | 8.7 |
| 7 | 17.31 | 5.12 | 11.8 | 18.2 |
| 8 | 17.80 | 4.98 | 5.6 | 26.6 |
| 9 | 18.16 | 4.88 | 2.2 | 1.8 |
| 10 | 18.83 | 4.71 | 1.6 | 2.1 |
| 11 | 21.47 | 4.13 | 0.9 | 0.5 |
| 12 | 22.06 | 4.03 | 12.5 | 13.8 |
| 13 | 22.40 | 3.97 | 2.2 | 2.4 |
| 14 | 23.09 | 3.85 | 2.6 | 2.0 |
| 15 | 23.74 | 3.74 | 1.8 | 1.6 |
| 16 | 25.83 | 3.45 | 1.5 | 1.8 |
| 17 | 27.30 | 3.26 | 7.2 | 9.6 |
| 18 | 27.51 | 3.24 | 7.1 | 14.1 |
| 19 | 28.29 | 3.15 | 5.7 | 6.4 |
| 20 | 29.53 | 3.02 | 1.7 | 1.9 |
| 21 | 30.88 | 2.89 | 0.8 | 1.0 |
| 22 | 34.51 | 2.60 | 1.2 | 1.2 |
| 23 | 35.37 | 2.54 | 0.5 | 0.6 |
| 24 | 37.21 | 2.41 | 2.4 | 2.4 |
| 25 | 38.27 | 2.35 | 0.8 | 1.4 |
| 26 | 40.53 | 2.22 | 0.5 | 0.8 |
| 27 | 41.40 | 2.18 | 0.3 | 0.3 |
| 28 | 42.09 | 2.15 | 1.1 | 1.1 |
| 29 | 45.96 | 1.97 | 2.8 | 3.2 |
| 30 | 46.67 | 1.94 | 0.5 | 0.7 |
| 31 | 56.49 | 1.63 | 0.3 | 0.5. |

5. An active pharmaceutical ingredient, comprising the crystalline forms of pinocembrin according to claim 1 or 4 as active ingredient.

6. The active pharmaceutical ingredient according to claim 5, daily dosage thereof ranges from 5 to 250 mg, based on the crystalline form solid of pinocembrin.

7. A pharmaceutical composition, comprising therapeutically effective amount of crystalline form of pinocembrin according to claim 1 or 4, in combination with one or more pharmaceutically acceptable carriers.

8. A dosage form, comprising the active pharmaceutical ingredient according to claim 5, characterized in that the dosage form is tablet, capsule, pill, injection, sustained-release preparation or controlled-release preparation.

9. A method for preparing β crystalline form of pinocembrin, comprising the steps of:
using α crystal form of pinocembrin as material, then obtaining β crystalline form of pinocembrin through
(a) crystal transition by grinding, or
(b) dissolving the material completely in a solvent of pyridine or DMSO, adding water to allow precipitate, and performing filtration under reduced pressure, freeze-drying or cold spray.

\* \* \* \* \*